United States Patent [19]

Slimak

[11] Patent Number: 4,946,703
[45] Date of Patent: Aug. 7, 1990

[54] PROCESSES FOR PRODUCTS FROM TRUE YAM

[76] Inventor: Karen M. Slimak, 9207 Shotgun Ct., Springfield, Va. 22153

[21] Appl. No.: 825,659

[22] Filed: Jan. 31, 1986

[51] Int. Cl.$^5$ .................... A23L 1/214; A23L 1/216
[52] U.S. Cl. .................................. 426/637; 426/385; 426/518; 426/520; 426/523; 426/524; 426/552; 426/601; 426/602; 426/640
[58] Field of Search ............... 426/94, 518, 520, 637, 426/523, 524, 640, 552, 562, 601, 602, 615, 385

[56] References Cited

U.S. PATENT DOCUMENTS

| | | | |
|---|---|---|---|
| 91,554 | 6/1869 | Marshall | 426/637 |
| 310,927 | 1/1885 | Whitcomb | 426/637 |
| 1,571,945 | 2/1926 | Heimerdinger | 426/550 |
| 3,881,028 | 4/1975 | Capossela et al. | 426/637 |
| 4,520,034 | 5/1985 | Ishii et al. | 426/96 |

FOREIGN PATENT DOCUMENTS

| | | |
|---|---|---|
| 1517050 | 8/1974 | Fed. Rep. of Germany . |
| 2950315 | 6/1981 | Fed. Rep. of Germany . |
| 3141174 | 4/1983 | Fed. Rep. of Germany . |
| 1395654 | 2/1964 | France . |
| 2574633 | 6/1986 | France . |
| 104850 | 8/1980 | Japan .................................. 426/639 |

OTHER PUBLICATIONS

Talburt et al., "Potato Processing", Avi Publishing Co., 1959, pp. 390–391.
Casier et al., "Bread Production from Pure Flowers of Tropical Starchy Crops", Trop. Foods Chem. Nutr., Inglett et al. editors, 1979, vol. 1, pp. 279–340.
Alice Bell and Jean-Claude Favier, Effect of Traditional Food Processing Methods of the Nutritional Value of Yams in Cameroon, in Tropical Root Crops: Research Strategies for the 1980s, 1980, p. 218.
Corwin, A. H., The Rotating Diet and Taxonomy, in Clinical Ecology, ed. L. H. Dickey, 1976, Charles C. Thomas Publisher, pp. 126–133.
The Oxford English Dictionary, 1933, Oxford, at the Clarendon Press, vol. VIII, pp. 1315, 1318.
Ware, Possibilities in New and Extended Uses of the Sweet Potato, 1941, pp. 1–12.
Beattie, W. R., 1908, Sweet Potatoes, U.S. Department of Agriculture, Farmers' Bulletin 324, pp. 35–37.
Watt, B. K., Merrill, A. L. Composition of Foods, Agriculture Handbook No. 8, U.S. Department of Agriculture, 1963, pp. 51, 66–67.
Gove, P. B., ed., Webster's Third New International Dictionary of the English Language Unabridged, Merriam-Webster Inc., Springfield, Mass., U.S.A., 1961, pp. 637, 1351, 2646.
Casier, J. P. J., et al., Bread Production from Pure Flours of Tropical Starchy Crops: III from Pure and Mixed Flours of Cassava, Millet, Sorghum, Corn, Rice, and the Starches, in Inglett, G. E., and Charalambous, G. eds., Tropical Foods: Chemistry and Nutrition, vol. 1, Academic Press; N.Y., 1979, pp. 279–340.
Ciacco, C. F., Tubers: Composition and Use in Bread Baking, Thesis, North Dakota State University School of Agriculture and Applied Science, 1977, 104 pp.
Casier, J. P. J. Effect of Water-Insoluble Endosperm Pentosans of Wheat and Rye on the Dough and Baking Properties of Soft Wheat and Other Starch-Rich Materials such as Manioc, Sorghum, Millet, etc. Fermentatio, vol. 71, No. 3, pp. 117–134, 1975, Translated from Dutch for the SEA, USDA, and NSF, by Saad Publications, Karachi, Pakistan.
Hudson, B. J. F. and Ogunsua, A. O., The Effects of Fibre, Starch Damage and Surfactants on the Baking Quality of Wheat/Cassava Composite Flours, Journal of Food Technology, pp. 129–136, vol. II, No. 2, 1976.
Crabtree et al., The Breadmaking Potential of Products of Cassava as Partial Replacements for Wheat Flour, J. of Food Techn., pp. 397–407, vol. 13, 1978.
Martin, F. W. Tropical Yams and Their Potential, Part 1. *Dioscorea esculenta*, Agriculture Handbook No. 457, pp. 16–18, 1974.
Martin and Ruberté, Flours Made from Edible Yams (Dioscorea spp.) as a Substitute for Wheat Flour, Journal of Agriculture of University of Puerto Rico, v. 59, pp. 255–263, 1975.
Martin et al., Introduction of Flour from *Dioscorea dumetorum* in a Rural Area, in Tropical Root Crops: Production and Uses in Africa, pp. 161–163, 1983.
Ensminger et al., editors, Foods & Nutrition Encyclopedia, Pegus Press, p. 2359, 1983.
Chemical Abstracts, vol. 99, No. 13, Sep. 1983, p. 485, Abstract No. 103962p, Columbus Ohio, U.S.; A. Sanchez Marroquin: "Two Forgotten Crops of Agroindustrial Importance: Amaranth and Quinoa", & Arch. Latinoam., Nutr. 1983, 33(1), 11–32.
Ciacco "Tubers: Composition & use in bread making" Diss Abst. Int B 1977 38(4).
Webster's Third New International Dictionary from (Editor) Merriam Co. Publisher 1961 pp 637, 2646.

*Primary Examiner*—R. B. Penland
*Attorney, Agent, or Firm*—Stevens, Davis, Miller & Mosher

[57] ABSTRACT

A variety of different food products, prepared from tuberous varieties of the true yam family, Dioscoreaceae, are substitutes for wheat and other grains, milk, eggs, and a partial substitute for nuts.

16 Claims, No Drawings

PROCESSES FOR PRODUCTS FROM TRUE YAM

BACKGROUND OF THE PREFERRED EMBODIMENTS (1) Field of Invention

The present invention is concerned with the utilization of tubers of the true yam and all other plants producing tubers in the family Dioscoreaceae, with the purpose of producing various flours from the tubers, and other valuable edible products and industrial products.

(2) Description of The Background

To increase the number of food products and forms of food products is of the greatest importance to persons with food allergies, and will become of even greater importance as food allergies are diagnosed in increasing numbers of people. As the potential problems of food allergies are more recognized, increasing numbers of people are looking for non-wheat items to include in their diets, to increase variety and aid in the prevention of food allergies.

Food allergies and intolerances have been known to exist for hundreds of years. The symptoms vary with each individual, and can include congestion, asthma, diarrhea, headaches, dizziness, joint pains, hives, eczema and in the most severe cases can cause anaphylaxis and even death. In recent decades, along with most other diseases related to the immune or auto-immune system, the incidence of food allergies has increased. In addition the number of foods to which a given individual reacts, and the severity of the reactions seems to be increasing. Indications are that food allergies/intolerances will continue to become increasingly more common and severe.

The need for new food sources and alternatives parallels the increase in food allergies. As the number of foods an individual can eat begins to dwindle, it becomes increasingly more difficult to maintain a nutritious, well-balanced diet from the foods remaining, and the search for new foods intensifies. For many food allergy patients, the allergy problem steadily becomes more severe as the patient is unable to avoid becoming malnourished.

There is, then, a real need for alternatives to the food products that are the common and accepted staples in the American diet. These food products need to be from hypoallergenic foods so they have the best chance of being well tolerated by the greatest numbers of people. The hypoallergenic food products need to provide acceptable substitutes for the most hyperallergenic food products - wheat, corn, and other members of the grass family, legumes, milk and milk products, eggs, nuts, and yeast.

The alternative food products should be from less common or less well known foods. Such foods will have been eaten less often, if at all, and there will be a lower chance for a person to have developed allergies to the new foods. Products from such uncommon foods could probably be tolerated by most persons, and the risk of developing allergies to the foods would be low.

The alternative food products need to be developed from foods in separate food families. This is important because food allergy patients can easily develop allergies to foods that are closely related to the foods they are already allergic to. New food products from as many new food families as possible (for example true yam products from the yam family). Dioscoreaceae are much more needed than are food products from uncommon foods in a common food family (such as millet from the grass family). Alternative food products from food families not frequently included in peoples' diets will increase substantially the foods that people can eat in their rotation diets.

The alternative food products need to be highly concentrated foods. The above list of hyperallergenic foods includes most of the concentrated carbohydrates in the normal American diet. When people have to exclude these foods from their diets, the plant sources they have left to eat are primarily green leafy vegetables, tubers, and fruits. These food sources are high in fiber, but are relatively low in carbohydrates. A person who must rely on potatoes or true yams as their main source of carbohydrates, must eat about 5 pounds each day. It is very hard for many adults to eat this much food, but it is even more difficult for allergic children who may have to eat almost as much.

The alternative food products need to be as close to the eliminated foods as possible, in form and texture. For example, breads, pastas, cereal, cookies are needed from hypoallergenic sources, and these need to be as similar in taste and texture as possible. This will make it possible for persons to enjoy foods they are used to, and will make them more likely to stay on their diets. Also people who are concerned that they may have food allergies are more likely to seek medical treatment if they know they will have pleasant alternatives in their diets.

Alternative food products are needed that consist of one primary ingredient, and this ingredient serves to replace wheat and other grains, milk, eggs, nuts, yeast, and sugar. The food allergies of individuals vary so greatly, that as the number of ingredients in a product increases, the number of individuals that can use the product decreases. Similarly, the products need to be free of additives, preservatives, and so forth, and should be completely free of pesticides and other chemicals.

Other characteristics that are important in new food products include convenience, portability, and variety. Many patients must change their diets at a time when they are very ill, and they simply do not have the strength to perform the food preparation needed when working with fresh fruits and vegetables.

Until now there has been no alternative food product which could meet all of the above criteria. Many food products have been developed, but essentially all contain either wheat, or other grains, soy or legumes, milk, eggs, nuts, yeast, or sugar, or they don't have the characteristics of the common food products. Many specialty flours such as amaranth, have been combined with wheat flour to make new products, and these are not useful to the food allergic patient. Until now, there has been no attempt to completely replace heat products with a non-grain flour source that also does not contain other main ingredients such as eggs, milk, sugar, and yeast. There appear to be no clear references to true yam varieties in the patent literature.

Previous products of true yam flour were dark grey and nonuniform in color, were susceptible to spoilage during dehydration, and produced inferior products that spoiled easily. It has been found that a flour can be prepared with a creamy-white, uniform color that has improved storage capability, and improved palatability.

SUMMARY OF THE INVENTION

It is on object of the present invention to provide flours and advantageous processes for producing flours from the true yam and all other tuberous varieties in the family Dioscoreaceae.

Another object of the present invention to provide advantageous processes of producing valuable products from the flours of the true yam, and all other varieties in the family Dioscoreaceae.

Another object o the present invention is to provide edible compositions of matter from the flour of all tuberous varieties of family Dioscoreaceae.

Another object of the present invention is to provide edible compositions of matter from the flour of all tuberous varieties of family, Dioscoreaceae.

Another object of the present invention is to provide advantageous processes for producing substitutes for wheat products and other grain products.

Another object of the present invention is to provide advantageous processes for producing substitutes for milk.

Still another object of the present invention is to provide advantageous processes for producing substitutes for products containing eggs.

Still another object of the present invention is to provide advantageous processes for producing substitutes for legumes and legume-containing products.

Another object of the present invention is to provide advantageous processes for producing substitutes for nut butter products and products containing nut butters.

Another object of the present invention is to provide advantageous processes for producing substitutes for wheat, other grains, legumes, eggs, milk, and yeast-containing products using true yam flour as essentially the only ingredient.

Still another object of the present invention is to provide novel and advantageous processes for producing the following products with true yam flour as the only ingredient other than water, oil, salt, and leavening agent: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, corn bread, pie crust, pizza dough, doughwrapped products, doughnuts, dumplings, hush puppies, and pretzels. Batter, milk, ice cream, milk shake, puddings, custards, light and heavy creams, condensed milk, muffins, waffles, french toast, crepes, and dry mixes for many products.

Another object of the present invention is to provide novel and advantageous processes for producing the following products with true yam flour as a primary ingredient: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, corn bread, pie crust, pizza dough, doughwrapped products, doughnuts, dumplings, hush puppies, pretzels, batter, milk, ice cream, milk shake, puddings, custards, light and heavy creams, condensed milk, muffins, waffles, french toast, protein coating batter, crepes, and dry mixes for many products.

Another object of the present invention is to provide advantageous processes for producing infant formulas.

Another object of the present invention is to provide advantageous processes for producing pharmaceutical products that are more effective for allergy patients with the use of hypoallergenic flours such as true yam flour as an inert ingredient.

Another object of the present invention is to provide advantageous processes for producing cosmetics containing true yam powder as cosmetic base and facial powder, and other uses.

Briefly, these objects and other objects of the present invention as hereinafter will become more readily apparent can be attained by a plurality of method embodiments which employ a flour obtained from true yam tubers to prepare a variety of different foodstuffs.

DETAILED DESCRIPTION OF THE PREFERRED EMBODIMENTS

The words "true yam" as used in this patent application are intended to include the name and cush-cush, and all other tubers in the family Dioscoreaceae.

It has now been found that flour from true yams and other tuberous plants in the family, Dioscoreaceae can be used in the production of many food products.

The true yam also called name, true yam, cush-cush, and mapuey and so forth is a tuber that varies in size from smaller than a potato to 100 pounds and more. Several varieties include, black, yellow and white. The outside skin may be reddish-brown, brown, grey, or black and so forth. This variety is not well known in the U where it is used primarily by people from Central and South America in the traditional ways of their homelands. In these countries the fresh tuber is used in almost any way a white potato is used—baked, fried (but will be very bitter), boiled, mashed. The true yam also has been processed for the starch which is used as a thickener.

In the work with true yams, flour was made from the process described below. We began product development by following recipes for wheat flour, and making substitutions according to standard formulas given in allergy cookbooks for egg and milk replacers. The result was resound failures. Wheat-based processes could not be readily adapted for use with the new flour and were abandoned.

In the first embodiment, a flour or flour-like substance is made in processes involving optional peeling by any conventional means, optional rinsing, trimming, optional cooking steps, optional shredding or otherwise comminuting to any desired size, drying by any means that avoids introducing a bitter taste into the flour such as air drying, freeze drying, vacuum drying, and the like, and pulverizing the dried products under and conditions that would not heat or otherwise change the particles sufficiently to introduce a bitter taste into the flour. These steps may be taken in any desired combination, in any desired order, including simultaneously.

Preferably, the tubers are peeled and trimmed to remove spots, worm holes, molded or spotted sections and the like, while being held under running water, rinsed in distilled water, cut into cubes of any size, preferably 2×2×2, and subjected to heat with steam until thoroughly gelatinized. The tubers are then trimmed to remove all black, grey or otherwise discolored sections, shredded to sizes approximately 2 inches long ×¼ inch wide ×⅛ inch thick, placed on glass trays and air dried at 145 F. for about 12 hours. The dried product is then pulverized to a flour of various particle size distribution in a low temperature grinding process.

In another preferred embodiment, the tubers are peeled as described above or otherwise comminuted shredded to any desired size, dried by freeze-drying or other vacuum drying methods, pulverized to flour of various particle sizes by any method that does not raise the temperature of the flour or otherwise alter it sufficiently to introduce bitter taste.

A cereal substance or constituent of cereal may be prepared from the dried shreds or particles of any shape of the true yam tuber which are shreds optimally may be roasted, baked, toasted (with or without oil), otherwise heated by any desired conventional technique.

A particulate material which is useful as a cereal substitute for the likes of cream of wheat can be prepared by pulverizing dried true yam tubers to particle sizes ranging from 0.3 inch to 0.02 inch, preferably 0.06 inch. The tuber may be peeled or unpeeled before processing; peeled tubers are preferred.

A bread product can be prepared from true yam flour, water, and a small amount of salt (optional), oil (optional), and any conventional leavening agent in proportions ranging from $1:\frac{1}{2}$ to 1:4, by weight, preferably 1:1.38 in processes of mixing at any desired speed, preferably a moderately high speed, shaping, and baking in any desired order or combinations of techniques common to the art. The true yam bread is baked at temperatures ranging from 275-550 F., preferably 425 F. for 15-90 minutes, preferably 50 minutes. The bread may also be prepared with any desired combinations of conventional ingredients including but not limited to other flours, extenders, binders, fillers, preserving agents, sweeteners, flavorings, seasonings, eggs, milk, nuts, and so forth.

In still another embodiment the bread product described above, and products such as corn bread, cookies, pancakes, muffins, and the like described in examples which follow may be used to prepare bread crumb and crouton-type and other similar products. Breads and the other products, in processes including but not limited to various orders and combinations of drying, toasting, coating, cutting, slicing, comminuting, and the like in steps conventional to the art may be used to produce bread crumb products with all possible uses of any other bread crumb products. These uses include but are not limited to: coating mixes for use alone or with batters, salad toppings, pie crusts, stuffings, and the like. They may also be prepared with any desired combinations of conventional ingredients including but not limited to other flours, extenders, binders, fillers, preserving agents, sweeteners, flavorings, seasonings, eggs, milk, nuts, and so forth.

By techniques in any desired order or combination of slicing, drying, roasting, toasting, baking, and the like, cubed products called croutons may be produced. These may be used on salads, soups, stews, stuffings, and any other ways croutons are used. The bread crumbs and croutons may also be prepared with any desired combinations of conventional ingredients including but not limited to other flours, extenders, binders, fillers, preserving agents, sweeteners, flavorings, seasonings, eggs, milk, nuts, and so forth.

In another embodiment, a corn bread- like product can be prepared from true yam flour, water, oil, and small amounts of salt (optional), sweeteners (optional), and of any conventional leavening agents in proportions ranging from $1 : 6 : \frac{1}{3}$ to $1: \frac{1}{2} : 0$, by weight, preferably $1 : 1 \frac{1}{2} : 1/24$ with processes of mixing at any desired speed, preferably a moderately high speed, shaping, and baking in any desired order or combinations of techniques common to the art. The true yam corn bread is baked at temperatures ranging from 275-550 F., preferably 425 F., for 15-90 minutes, preferably 50 minutes. When a liquid sweetener such as a honey is used, the proportions range from $1 : 6 : 2 : \frac{1}{3}$ to $1 : \frac{1}{2} : 0 : 0$, preferably $1 : 1.2 : 0.2 : 0.04$ of true yam flour, water, honey, and oil. The corn breadlike product may also be prepared with any desired combinations of conventional ingredients including but not limited to other flours, extenders, binders, fillers, preserving agents, sweeteners, flavorings, seasonings, eggs, milk, nuts, and so forth.

In another embodiment, a cake dough product can be prepared, in the method described above for corn bread by increasing ranges and preferred amounts: the amount of oil by 100%, increasing the amount of honey by 20%, and increasing the amount of baking powder by 25-50%. Alternatively, honey may be omitted. These doughs produce a baked cake-like product without added ingredients, although ingredients commonly used in the art may also be incorporated into the dough or added to the finished products. The cake may also be prepared with any desired combinations of conventional ingredients including but not limited to other flours, extenders, binders, fillers, preserving agents, sweeteners, flavorings, seasonings, eggs, milk, nuts, and so forth.

In still another embodiment by the processes described for corn bread products, muffins may be produced. The range of ratios of flour, water, and oil are the same as for the corn bread product, with preferred proportions of $1 : 1 \frac{1}{2} : 1/24$.

In another embodiment, products the likes of pancakes, doughnuts, hush puppies, batter, crepes can be prepared from combinations of uncooked true yam flour, water, oil, and small amounts of salt (optional), sweeteners (optional), and of any conventional leavening agents in proportions virtually identical to those for corn bread. The ranges of general proportions are identical with preferred proportions being $1 : 1 \frac{1}{2} : 1/12$. For cooked true yam flour, proportions of frozen flour, rapidly boiling water, and oil range from $1 : 6 : 1$ to $1 : \frac{1}{2} : 0$, preferably $1 : 2.7 : 1/5$. These products are mixed, molded, shaped, fried, and so forth as appropriate for the product. The pancakes, doughnuts, hush puppies, batter, and crepes may also be prepared with any desired combinations of conventional ingredients including but not limited to other flours, extenders, binders, fillers, preserving agents, sweeteners, flavorings, seasonings, eggs, milk, nuts, and so forth.

In still another embodiment the above described pancake batter prepared as described earlier may be used as a pizza dough. In processes involving pouring the batter onto an appropriately shaped or sufficiently large surface, heating or baking in temperatures ranging from 375-525 F., preferably 425 F., until dough is almost done but still tacky on the top, about 20 minutes. Add any desired ingredients including but not limited to various meats, cheeses, vegetables, spices, and other materials common to the art. Although any ingredients may be used, hypoallergenic ingredients might include ground precooked venison and nopales. Bake until dough is completely done and ingredients thoroughly cooked, about 10 minutes.

Alternatively, the toppings described above may be placed on the batter before cooking begins.

Alternatively, the above dough may be thoroughly baked, toppings added, and pizza reheated.

Alternatively the dough described for pie crust may be used as a pizza dough. The dough is prepared as described in the example, the dough is rolled out to the desired length, width, and thickness, toppings of any kind are added and the mixture is baked at 350 F. for 10-30 minutes.

In yet another embodiment, a product such as waffles can be prepared from true yam flour, water, oil, and small amounts of salt (optional), sweeteners (optional), and any conventional leavening agent in proportions similar to those described previously for corn bread. The ranges of general proportions are identical to that for corn bread, with preferred proportions being 1 : 1 ⅔ : 1/12. Processes of combining ingredients and batter preparation are as described for cornbread. Batter is then placed in waffle irons or other type of molds and heated by conventional means.

In another embodiment, a product such as french toast batter can be prepared from true yam flour, water, oil, and a small amount of salt (optional) in proportions ranging from 5 : 12 : 8 to 1/10 : 12 : 0 by weight, preferably 1 : 12 : 2 in processes of gelatinizing the flour and water mixture, combining with remaining ingredients and blending with high speed blending equipment until smooth and homogenous. Material to be coated and prepared for french toast is preferably true yam bread, although any other bread or bread-like product may be used, and cooking is by any accepted technique.

Alternatively batter may be prepared by the method above omitting the step of gelatinizing the flour-water mixture. Alternatively, proteinaceous material may be added in proportions ranging from 0-8 parts per 12 parts flour, 2 parts proteinaceous material per 12 parts flour are preferred. The batter may be used alone, or in combinations with bread crumbs and other coating materials. The batter may also be prepared with any desired combinations of conventional ingredients including but not limited to other flours, extenders, binders, fillers, preserving agents, sweeteners, flavorings, seasonings, eggs, milk, nuts, and so forth.

In another embodiment, a product such as cookies can be prepared from uncooked true yam flour, water, oil, small amounts of salt (optional), sweeteners (optional), and small amounts of an conventional leavening agents in proportions ranging from 4 : 1 : 0 to 0.5 : 1 : 2, by weight, preferably 1.8 : 1 : 0.9 in processes of mixing, kneading, shaping, baking to produce cookies. If cooked true yam flour is used proportions are 4 : 1 : 0 to 0.3 : 1 : 1 , preferably 0.75 : 1 0.3 of frozen flour, boiling water, and oil. Baking conditions range from 275 - 500 F, preferably 400 F., and 2-40 minutes, preferably 8-10 minutes.

Alternatively, when a liquid sweetener is used, the proportions are within the ranges described above, preferably 1 : 1.5 : 0.3 and 0.24 parts honey or other liquid sweetener per 1 part flour. Sweetener amounts may range from 0-1 part per 1 part flour.

Alternatively, add toppings as desired to the unbaked or baked dough. Any desired fruit, nuts, flavors, seasonings, sweeteners of the conventional art may be incorporated. The cookies may also be prepared with any desired combinations of conventional ingredients including but not limited to other flours, extenders, binders, fillers, preserving agents, sweeteners, flavorings, seasonings, eggs, milk, nuts, and so forth.

In yet another embodiment, crackers may be produced in any suitable machine for mixing heavy doughs through processes involving combining flour, water, and oil in proportions ranging from 3 : 1 : 4 to ½ : 1 : 0, preferably 1 : 0.7-1 : 1/6 parts flour, boiling water, and oil and small amounts of salt and leavening agents. In processes including but not limited to molding, rolling, cutting, and extruding, shape dough into desired cracker shapes. Dough may or may not be coated with a thin film of oil and salt. Any conventional heating method may be used, preferably 350 F. for 20 minutes. The crackers may also be prepared with any desired combinations of conventional ingredients including but not limited to other flours, extenders, binders, fillers, preserving agents, sweeteners, flavorings, seasonings, eggs, milk, nuts, and so forth.

In another embodiment of the invention a product such as tortillas or chips can be prepared by blending true yam flour with water, and then baking the appropriately shaped dough. In preparing the mixture a range from ¼ : 1 to 4 : 1 amounts of flour and water are blended, preferably 2 to 1 flour and water. The dough may be cooked by any desired means including but not limited to frying with or without oil, and baking with or without a thin film of oil, following the conventions of the art.

In still another embodiment of the invention, a food product such as pie crust is prepared by blending true yam flour and oil in relative amounts of 0.2 to 1 ½ parts water per unit part flour, preferably 0.5 part water per one part flour, and 0.1 to 1 part oil per unit part flour, preferably 0.3 parts oil per one part flour. Once the blend is prepared, it is kneaded, shaped or molded and baked if desired at temperatures ranging from 275 to 500 F., preferably 350 F. for from 2 to 45 minutes, preferably 10 minutes.

In yet another embodiment of the invention, pretzels may be prepared from the doughs described for tortillas, chips, and pie crusts in processes of shaping, optional salting, and various combinations of baking with or without a thin coat of oil, broiling, steaming, drying common in the food art to produce a pretzels of desired sizes and shapes. Additional embodiments include the pretzels above to which have been added to dough before baking or to the outside surface before or after baking, a variety of fillers, extenders, binders, flavorings, seasonings, preservatives and the like common to the art.

In yet another embodiment, the thick dough produced by the processes described in the preparation of pie crust may be used to produce dough encased or wrapped food products. The kneaded, thoroughly mixed dough may be shaped by extruding, rolling, cutting, and any other convenient technique to produce a variety of shapes onto which pureed fruit, chopped meats, hot dogs, meat and vegetable combinations, cheese and the like may be placed. For example the thick dough may be shaped into 3×3×¼ inch squares onto which a pureed fruit such as sapote or carambola, and any other unusual or common fruit, are placed. These may be baked, or broiled, as is or 2 squares may be placed together such that the fruit forms a middle or inside layer in a sandwich-type effect. This may be baked, broiled, or fried to produce a product or may be frozen for sale to the consumer as a frozen product.

In another example, conventional art may be used to completely encase fruit or meat and vegetable mixtures. The dough covered product which may have any shape, commonly an ovoid shape ranging from 1 inch to 6 inches in length may be baked, boiled, broiled, and so forth in any conventional means to produce good tasting, convenient foods.

The dough may also be used in pot pie-type products.

In another example, pureed or flaked meat may be combined with a small amount of imitation mayonnaise in approximate proportions of 2 : 1 and placed on a 6×6×¼ inch dough square. The dough is rolled around the meat mixture to form a tamale-like shape. This product may be baked, broiled, fried, or frozen. If uncooked meats are used, the product should be cooked by means other than frying. The dough-wrapped products may also be prepared with an desired combinations of conventional ingredients including but not limited to other flours, extenders, binders, fillers, preserving agents, sweeteners, flavorings, seasonings, eggs, milk, nuts, and so forth.

In another embodiment, true yam flour may be combined with a vegetable oil such as sunflower oil, olive oil, or the like in an amount ranging from 1:1 to 1:4 parts by weight oil per part by weight flour, preferably 1:2.3, to which is added from 1/25-½ parts gelatinized water-flour mixture per part flour, preferably 1/20:1, in processes to produce a product very similar to nut butter in taste and consistency.

The true yam flour may be combined with various ingredients to prepare a colloidal product having the consistency of mayonnaise. The mayonnaise-like product itself is rather bland in taste, and it takes on the flavoring characteristics of the material(s) blended with it in its end use—e.g. tuna fish, potato salads, sandwich meats. Flour, water, and oil are combined in ratios of 1 : 4:–12 : 0.5–10, preferably in ratios of 1:8.5:3.8. The flour and water are combined and heated by any convention of the art to such temperature and for sufficient time to completely gelatinize the starch granules. This mixture in steps of cooling and high speed blending with remaining oil to produce a colloidal product to which may be added any acid, such as lemon juice, citric acid, ascorbic acid, acetic acid and the like in amounts ranging from 0–2 parts acid to 1 part original flour used, about 0.6:1 is preferred.

The mayonnaise has the colloidal properties of mayonnaise, with no other added ingredients. This is not to preclude the use of other ingredients commonly used in the food art, including but not limited to eggs, milk, other flours and starches, sweeteners, flavors, seasonings, and spices of any kind. The mayonnaise produced by the above processes has the advantages of being able to be frozen and thawed without destroying or significantly altering the colloidal properties of the product.

In another embodiment of the invention, custard-type products may be produced. When flour and water are combined in proportions ranging from 1 : 1 to 1 : 30, preferably 1 : 6, and heated with stirring until gelatinized to a thick paste-like glue and subjected to blending in high speed blending device with the addition of oils in proportions ranging from 0 : 1 to 3 : 1, preferably ⅓ part oil per 1 part original flour by weight, this process produces white, creamy fluids of various thicknesses with properties similar to evaporated milk, which when allowed to stand with or without cooling, will solidify to produce products with properties very similar to custards. These custard-type products may be used without modifications as custards. In another embodiment the fluids may be combined with vegetables such as peas, corn, and squash to form custards commonly called corn puddings and the like. The fluid may be combined with pureed vegetables such as corn, pumpkin, and squash to produce custard-like pies, and with fruits such as peaches, apricots, coconut, and bananas to form creamed pies and the like.

One of the advantages of these products is that they do not require further cooking to produce the "setting up" and when combined with precooked vegetables, etc. do not need additional baking or other heat treatments. The custards may also be prepared with any desired combinations of conventional ingredients including but not limited to other flours, extenders, binders, fillers, preserving agents, sweeteners, flavorings, seasonings, eggs, milk, nuts, and so forth, but they are not necessary to achieve the desired product.

In another embodiment of the invention, a product such as a pudding can be prepared by blending flour, water, and pureed fresh, cooked true yam in proportions ranging from 1/100 : 1 : 1/6 to 1 : 1 : 5, preferably about 1/27 : 1 : .8. The product is produced in processes where as a first process step the flour and from 3 to 100%, preferably 10-50% of the water are combined and heated by any convention of the art to produce a thick gelatinized paste. This paste is then combined with the remaining raw materials and blended to a smooth, homogenous, mixture by conventional mixing techniques. Alternatively a pudding-type product may be prepared using flour and water only, in proportions ranging from 1 : 30 to 1 : 3 , preferably 1 : 10.6. The ingredients are combined, heated by any conventional techniques until the mixture completely gelatinized, cool to between 30 C or, preferably 10–20 C. until the consistency of pudding. With the addition of no additional ingredients the above products have a sweet, pleasant taste. However, this is in no way intended to preclude the use of other constituents commonly used in puddings including but not limited to an desired combinations of conventional ingredients including but not limited to other flours, extenders, binders, fillers, preserving agents, sweeteners, flavorings, seasonings, eggs, milk, nuts, and so forth.

In still another embodiment, in processes as are described for pancakes; flour, water, oil, baking powder, and salt are combined in proportions preferably of 6 : 11 : 1 : ½ : ⅛, but ranging from 8 : 12 : 1 : 1 : ½ to 4 : 5 : 1 : 0 : 0 to produce a crepe-type product. The batter may be used by techniques known to the art in cooking and using the true yam crepes. The may also be prepared with any desired combinations of conventional ingredients including but not limited to other flours, extenders, binders, fillers, preserving agents, sweeteners, flavorings, seasonings, eggs, milk, nuts, and so forth.

In still another embodiment of the invention, when a given amount of true yam flour is mixed with water of a temperature range from 0 to 150 degrees C., boiling water is preferred in proportions ranging from ½ to 4 parts of flour per part water, preferably 1 part flour to one part water, a dough can be prepared, which, after maintaining a heating and kneading period of from 0 to 10 minutes, preferably 1 minute, followed by extruding, cutting and drying, prepares such products as noodles, pastas and the like. It is also possible to mix the batter prepared with baked true yam or other farinaceous and mealy textured tubers and possibly other vegetable matter in the amounts to produce stiff doughs for gnocci, hard dumplings, and other pasta products. In another embodiment of the invention, a thick gelatinized paste of cooked true yam flour and water comprised of preferably 1 : 6 parts flour and water, with acceptable ranges of 1 : 2–30, may be added to the above described dough mixture before extrusion to any desired pasta shapes, to produce substitutes for egg based pasta.

In a further embodiment of the invention, the pasta doughs described above, with or without the egg-substitute may be heated at temperatures above 50 C. for 2-30 minutes, preferably 2-5 minutes at 95 C. to gelatinize a part of all of the dough prior to extrusion.

The pastas thus described are dried by any conventional means, preferably air dried on trays to produce a final product.

In its final uses, this pasta does not swell significantly beyond its dried size, when cooked in boiling water and the like. This is due to the fiber content which has been retained in the flour. These fibers prevent the typical swelling and conversion to a jelly-like mass common to noodles from most pure starches. Thus these pasta products retain a form and consistency similar to wheat based noodle products. They may be used in all ways any other noodles are used.

In another food embodiment, the true yam flour can be combined with water in a ratio of 12 : 1 to 3 : 1 parts by volume water per unit volume of flour, preferably 5.3:1 water to flour, and a small amount of a vegetable oil to produce a true yam milk. The ingredients are combined, thoroughly mixed in a high speed blending device to produce a true yam milk or other similar fluid mixtures.

In the above embodiment, flour of almost any particle size may be used ranging from very coarse to very fine. A more finely divided flour product is desired, preferably at least less than 0.001 inch. The milk produced from very fine flours does not require straining to yield a smooth homogenous product. Larger particle sizes produce a gritty product that must be strained before use. The larger the particle sizes, the greater proportion of true yam flour that is removed by straining, and the more separation into layers that occurs on setting.

In another food embodiment, true yam flour can be combined with water in a ratio of 1 : 1 to 30 : 1 parts by volume of water per unit of flour, preferably 5-10:1 water to flour, and a small amount of a vegetable oil. 50 to 100 per cent of the flour is combined, and heated until the mixture is completely gelatinized. The gelatinized mixture and remaining ingredients are combined, and thoroughly mixed in a high speed blending device to produce substitutes for light to heavy creams and condensed milk.

In another embodiment of the invention, true yam flour may be combined with water in amounts from 1 ½ to 1 : 6, preferably 1 : 1 ½, a small amount of oil, and crushed ice to prepare milk shake and ice cream-like products. From ¼ to ¾ of the flour, preferably ½ of the flour used is combined with water heated by any convenient means until thoroughly gelatinized, then combined with remaining flour, crushed ice, and a small amount of oil in a suitable blending device to produce a thick milk shake-like slurry product. The true yam milk shake has a pleasant taste without further additions, but may also be flavored with any fruits, nuts, sweeteners, or other flavors to produce many flavors and blends. The milk shake product may also be prepared with any desired combinations of conventional ingredients including but not limited to other flours, extenders, binders, fillers, preserving agents, eggs, milk, nuts, and so forth.

In another embodiment the above milk shake-like product may be used in processes of freezing, pulverizing, in one or two freezing and pulverizing cycles, to produce a product blended to a creamy consistency of ice cream. The true yam ice cream has a pleasant taste without further additions, but may also be flavored with any fruits, nuts, sweeteners, or other flavors to produce many flavors and blends. The ice cream product may also be prepared with any desired combinations of conventional ingredients including but not limited to other flours, extenders, binders, fillers, preserving agents, eggs, milk, nuts, and so forth. This product may also be used as an ingredient in more conventional ice cream preparations.

In other embodiments of the invention, the finely divided flour may be employed as a thickener, filler, or extender in the preparation of hypoallergenic cosmetics, and industrial products. For example, true yam flour of fine particle sizes may be used in dusting powders and face powders. Various shades may be obtained by heating and toasting methods. This produces a face powder product which is well tolerated because people would be only placing nonallergic items on their faces. The flour may also be used as bases for liquid and paste makeups and other cosmetic products to produce hypoallergenic products. The cosmetic preparations may also be prepared with any desired combinations of true yam flour with conventional ingredients including but not limited to other flours, extenders, binders, fillers, preserving agents, and so forth.

The flour from dried, cooked true yam of various particle sizes may be coarsely ground to produce a creamed cereal product and finely ground to produce instant mashed true yam products. In final use, each product is combined with water in ratios of 1 : 5-15, preferably 1 : 10 for creamed cereal and 1:7 for instant mashed true yam, heated for 2 to 10 minutes at temperatures from 75 to 100 C., preferably 100 C. in processes of rehydration and heating.

The cooked true yam flour may also be used in combination with the raw true yam flour in many of the products and processes described previously, and may also be used with many other types of flours.

Yet another embodiment involves processes to produce a hypoallergenic infant formula. Many infants are unable to tolerate the currently available infant formulas. Infants unable to tolerate the grains, legumes, milk products, eggs, and grain-derived sugar listed earlier along with coconut oil are almost certainly going to be intolerant of all commercially available infant formulas. These infants are usually unable to tolerate breast milk because of allergies to digested food residues in the milk. The parents of these infants desperately seek alternatives and usually end up using cooked purees of tubers and other foods. There is a real need for infant formulas without grains, grain-based sugars, legumes, milk and milk products, and coconut or corn oil. No truly hypoallergenic formula exists at present.

The earlier described process for producing true yam milk from precooked flour may be used to produce infant formulas. In another process the raw tubers are cooked to a thick gelatinized mash, mass pureed at high speeds to form a colloidal blend, which is combined with the milk product described above or used separately to form an infant formula. In one infant formula embodiment the just described formulas are used without further modification in either full fluid form, condensed form, or dry powdered form as a hyperallergenic formulas to which the user would add pureed, cooked protein in the amount of about 2.5 g protein per quart of fluid, and 40 g of fat per quart of fluid fully reconstituted. This would be ideal for many infants since the protein and fat sources could be varied by the parents according to the physician's instructions and specific allergies of the infant. This would assure the broadest tolerance of the formula.

The tubers such as true yams are highly nutritious in vitamins and minerals, and is therefore an excellent choice for hypoallergenic formulas.

In another embodiment of the invention, a more complete infant formula may be obtained by adding the previously described amounts of protein and carbohydrates to the above described formulas. Any protein and fat source is included in the embodiment as part of the product and process, preferably for hypoallergenic purposes beef, milk, pork, eggs, lamb, goat, and legume sources would not be used, obscure protein sources such as venison, rabbit, even fish are much, more suitable, as fat source sunflower oil is preferred although any oil or other desired fat source can be used. By conventions of the art formula available as ready-to-feed, liquid concentrate, and dry powder, and any other form are included in the embodiment.

Many variations in the above formula by varying amounts of oil, water, true yam, cooked versus uncooked flours, added ingredients and so forth, all are hereby included in the embodiment. The infant formula may also be prepared with true yam flour and combinations of conventional ingredients including but not limited to other flours, extenders, binders, fillers, preserving agents, sweeteners, flavorings, seasonings, eggs, milk, nuts, and so forth. These are hereby included in the embodiments.

In another embodiment, true yam flour may be used in a wide variety of pharmaceutical products as a hypoallergenic filler, extender, and inert ingredient. The use of a hypoallergenic material for these purposes would eliminate allergic reactions that food allergic patients may have to the nonactive ingredients, would thereby enhance the number of persons who tolerate the drugs and could help the medications to be more effective for the allergic patient.

Finally, to promote complete utilization of the entire true yam tuber, true yam may be used in processes to produce animal feed products. An animal feed is prepared by cooking and drying the peels of true yams (entire tuber if desired) by any of various methods, and then the peels are comminuted to a particle size ranging from ½-¼ inch to a powder by any conventional means desired. The comminuted material is then combined with from 2 to 40% of any suitable fatty material, 0-8% of any suitable protein source, and with vitamins and minerals added as desired. The substance obtained may be used directly as an animal feed, in ratios ranging from 5:1 to 1:100 with other animal feed products, preferably 1:5. Alternatively, the above true yam product may be combined with the remainder of the true yam plant, ie, dried comminuted leaves and vines to produce a feed.

Many of the products described above are well suited for the preparation of packaged dry mixes, frozen products and the like, all such products and processes are incorporated with this embodiment.

As is evident from the above discussion, the central objective of the present invention is to provide a variety of different foodstuffs, the basis for all of which is tuberous plants, of the family Dioscoreaceae. Thus, insofar as the flour obtained from the tuber is mixed with other ingredients which do not detrimentally affect the hypoallergenic properties of the food product obtained, hypoallergenic foodstuffs of different sorts can be obtained by the techniques described above. On the other hand, it is recognized that other ingredients can be added to the flour used in the present invention which may destroy the hypoallergenic nature of the food-stuff being produced, but yet which produce useful foodstuffs of still different qualities. The present invention also embraces these hyperallergenic foodstuffs, and therefore the present invention is not limited to just hypoallergenic foodstuffs.

Having generally described this invention, a further understanding can be obtained by reference to certain specific examples which are provided herein for purposes of illustration only and ar not intended to be limiting unless otherwise specified.

EXAMPLE NUMBER 1

True Yam Bread

Place 453 g true yam flour in a suitable conventional mixing device. Slowly add 623 g water and 3.25 g salt while mixing at lowest speed. When well blended mix, at highest speed for about 1 minute. Stir in 47 g baking powder; then mix at high speed for 15 seconds. As fast as possible pour into baking pan. Carefully place in oven heated to 425 F and bake for 50 minutes. The amount of water needed varies with the moisture content and particle size of the flour. More coarse flour and/or flour with a lower moisture content will require more water. The resultant true yam bread product may be used in any way wheat bread is used.

EXAMPLE NUMBER 2

True Yam Imitation Corn Bread

Ingredients: 304.8 g true yam flour, 453 g water, 23.6 g true yam baking powder, 6.5 g salt, 12.5 g oil. Combine above ingredients with baking powder added last; mix well, at highest speed with conventional mixing equipment until well blended and uniform consistency, about 1 minute. Transfer quickly into suitable baking container and bake 20-25 minutes at 425 F.

Alternatively, the following proportions may be used in an imitation corn bread with honey or other liquid sweetener: 343 g true yam flour, 396.4 g water, 6.5 g salt, 75 g honey, 23.6 g true yam baking powder, 12.5 g oil.

EXAMPLE NUMBER 3

Cake Dough 343 g true yam flour, 396.4 g water, 90 g honey, 35 g oil, 35.4 g suitable leavening agent, may be combined in the processes described in Example 2. Dough may be baked as described in Example 2, prior to baking or after, the cake dough may be prepared or finished with any desired combinations of conventional ingredients including but not limited to other flours, extenders, binders, fillers, preserving agents, sweeteners, flavorings, seasonings, eggs, milk, nuts, and so forth.

EXAMPLE NUMBER 4

True Yam Muffins

Combine 343 g true yam flour, 453 g water, 6.5 g salt, 12.5 g oil, 23.6 g true yam baking powder and mix well, at high speed with conventional techniques of the art until smooth and well blended. Add 23.6 g baking powder and mix well. Pour quickly or transfer by other means into suitable baking equipment. Bake for 20-25 minutes at 425 F.

EXAMPLE NUMBER 5

True Yam Pancakes

The following ingredients: 169.9 g frozen cooked true yam flour, maintained at freezing point 453 g rapidly boiling water, 0.5 g salt, 37.5 g oil, 12 g true yam baking powder, are combined and mixed well on highest speed, preferably 5 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color.

When honey or other liquid sweetener is used, the ingredients: 169.9 g true yam flour, 453 g water, 0.5 g salt, 37.5 g honey, 25 g oil, 12 g true yam baking powder, may be used in the process described above.

EXAMPLE NUMBER 6

True Yam Pancake Mix

To provide an example of a dry mix-type product, true yam pancake mix is used. A true yam pancake mix product can be made by combining ingredients: 453 g flour, 87 g salt, and 10.7 g true yam baking powder. Mix ingredients well in a rolling ball mill or other conventional means to form a dry mix. Pancakes can be made from this dry mix by the addition of water and water/oil mixtures.

Alternatively, by conventions of the art, the pancake mix oils may also be added to the above ingredient mix to produce a dry mix that contains oils. Also, sweeteners, flavors, seasonings, binders, fillers, and so forth may be utilized in the production of true yam pancake mixes.

EXAMPLE NUMBER 7

Pizza Dough

The batters described in Example 5 may also be used as a pizza dough. Prepare batter as described above, pour dough onto pizza pan. Place in oven and bake at 425 degrees until dough is almost done but still tacky on the top, about 20 minutes. Add any desired ingredients various meats, vegetables, spices, and other materials common to the art. Bake until dough is completely done and ingredients thoroughly cooked, about 10 minutes.

Alternatively, the topping can be placed on the batter before cooking begins, or after cooking ends. Alternatively, the dough described for pie crust, Example 15, may be used as a pizza dough. The dough is prepared as described in the example, the dough is rolled out to the desired length, width, and thickness, toppings of any kind are added and the mixture is baked at 350 F. for 10-30 minutes.

EXAMPLE NUMBER 8

True Yam Waffles

The following ingredients are combined by the method described above in Example 5: 304.8 g true yam flour, 509.6 g water, 6.5 g salt, 50 g oil, 3.6 g true yam baking powder. Pour batter into waffle iron or other suitable molding or shaping device preheated to 300-500 F. Watch for steam coming from the waffle iron as the waffles cook. Leave waffle iron closed as long as steam can be seen rising from the waffle iron. When steam stops, all water has been baked out of the batter and waffles are done, 5-10 minutes or more. When done the waffles should be golden brown in color.

EXAMPLE NUMBER 9

True Yam French Toast

Combine 226.5 g water and 21.2 g flour. Heat by any desired convention to form a thick paste. Coat pieces of true yam bread. Fry to slightly browned and crusty in lightly greased griddle or skillet preheated to medium high. Alternatively combine 19.05 g flour, 3.25 g salt, and 226.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely pulverized and liquefied.

Coat pieces of true yam bread. Fry to slightly browned and crusty in lightly greased griddle or skillet preheated to medium high. Alternatively french toast batter may be prepared by the method as described above without cooking the flour/water mixture.

French toast batter may be used for many combinations with true yam bread crumbs and many other coating materials or alone.

EXAMPLE NUMBER 10

True Yam Cookies

Combine and mix well on highest speed 1-10 minutes, preferably 2-3 minutes: 339.75 g true yam flour, 453 g rapidly boiling water, 0.6 g salt, 125 g oil, 12 g true yam baking powder. Form into cookie shapes by the conventional art. Bake at 400 F. on ungreased surface for 8-10 minutes, or until a light golden brown on the underside. Alternatively, add toppings as desired to the unbaked or baked dough. Any desired fruit, nut, flavors, seasonings of the conventional art may also be used.

When a liquid sweetener or honey is used, the following ingredients are combined as described above: 339.75 g frozen true yam flour, 453 g rapidly boiling water, 0.6 g salt, 75 g honey, 100 g oil, 12 g true yam baking powder.

EXAMPLE NUMBER 11

True Yam Doughnuts, Pretzels, Hush Puppies, Doughnut Holes

From batter prepared in the method of Example 5, extrude batter through a doughnut press or any other desired device in rings onto hot oil; batter may also be dropped in balls, long pieces, even pretzel shapes. Temperature of the oil should be about 300-500 degrees.

If the oil is hot enough the dough will float at the top of the oil. Fry doughnuts or other shapes until golden brown on all sides. Remove from oil, drain. Serve plain or top with fruit, honey, nuts, coconut, peanut butter, etc.

Alternatively, doughnuts may be preparations of conventional ingredients including but not limited to other flours, extenders, binders, fillers, preserving agents, flavorings, seasonings, eggs, milk, and so forth.

EXAMPLE NUMBER 12

True Yam Dumplings

Combine 152.4 g true yam flour, 226.5 g water, 4.9 g salt, 12 g true yam baking powder until smooth and creamy. Let dough set for about 15 minutes. Drop teaspoon-sized portions of batter into about 2 liters of rapidly boiling water or broth, may be thickened. Allow to remain in boiling water 2-6 minutes, preferably minutes. If dumplings remain in boiling broth longer, dumplings will dissolve. When done, dumplings will be light and tender on the inside.

EXAMPLE NUMBER 13

True Yam Batter

A batter prepared by the method of Example 5 may be used as batter for deep frying and for fondue cooking techniques. Coat vegetables, fruit, or cooked meat in batter and deep fry in hot oil (preheated to medium-high heat) If the oil is hot enough the dough should float at the top of the oil. Test for proper temperature with a small ball of dough.

EXAMPLE NUMBER 14

Crepes

In yet another embodiment of the batter prepared in Example 5, the batter may be used to make a crepe-like product. The batter may be diluted by the addition of 10-400 g. water, preferably 100 g. to make a crepe-like product. The batter is spread in very thin layers on a cooking surface, and prepared according to the accepted convention.

EXAMPLE NUMBER 15

True Yam Pie Crust

Mix thoroughly, 169.9 g true yam flour, 50 g oil, 85.2 g water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery.

True yam pie crust may be used as a double or single crust pie, with any type of filling, including meat (eg, chicken pot pie) or fruit filling. May be used baked or unbaked. For a baked pie crust bake for 10 minutes at 350 F.

Although above ingredients are preferred, true yam flour may be used with shortening or lard and any other conventional ingredients. For example, when using lard, use about 100 g and decrease water to 10-14 g. Dough will seem stiff and hard, but will be just right after baking.

EXAMPLE NUMBER 16

True Yam Tortillas, Chips

Mix 169.9 g true yam flour with 85 g boiling water; knead until well blended and very thick. By any desired conventional means achieve the shapes and sizes of tortillas or chips, bake at 350 F. for 10 minutes. When fried without oil, heat on medium high heat until slightly browned on both sides; turn as needed. When fried in hot oil, fry until crisp.

EXAMPLE NUMBER 17

Pretzels

Doughs produced by the processes described in Examples 15 and 16 may be used in processes of shaping to form pretzels of various sizes, coating with oil (optional), cooking by various processes of the art including but not limited to baking, and drying to produce pretzels of varying sizes.

In alternative processes, pretzels may be produced in processes above into which are incorporated any combinations of processes including but not limited to additional flours, eggs, milk, flavorings, seasonings, binders, fillers, extenders, and preserving agents.

EXAMPLE 18

True Yam Imitation Nut Butter 453 grams of true yam flour are placed into any blending equipment suitable for mixing very thick doughs at very high speeds, to which is added 150-200 g edible fatty material, such as vegetable oils (preferred for hypoallergenic products) but could also include other fatty materials. The materials are intimately mixed for about 2 minutes or until the entire mixture is well blended, and the consistency of nut butter. After several weeks of storage oil and flour will begin to separate, but is recombined very easily. Alternatively, the mixture may be heated until the true yam flour is partially gelatinized to produce an imitation nut butter that separates less easily.

EXAMPLE 19

True Yam Imitation Mayonnaise

Combine 53.1 g true yam flour, and 453 g cold water until well blended. Continue stirring, while maintaining temperature at 50 to 150 C., until mixture is completely gelatinized and thickened. Place mixture in conventional high speed blending device; add 200 g. oil, and optional: 21.3 g lemon juice, vinegar, or ascorbic acid solution. Mix materials on highest speed until well blended, smooth, and uniform consistency. Mayonnaise will thicken as it cools.

EXAMPLE NUMBER 20

True Yam Milk

Combine 906 g water and 169.9 g true yam flour, and 12.5 g oil, mix thoroughly. Blend 1-30 minutes at highest speeds, preferably 4 minutes. May be strained if flour not sufficiently fine.

EXAMPLE NUMBER 21

True Yam Milk Shake

Combine 76.2 g flour and 226.5 g water in suitable mixing and heating apparatus. As mixture approaches boiling point, increase revolutions per minute. Continue rapid stirring while boiling for about 5 minutes. When thoroughly gelatinized, very thick, and smooth, cool to 50 F or lower, preferably 35 F. In high speed blending device, combine gelatinized mixture, 12.5 g oil, 76.2 g true yam flour, and 226.5 g crushed ice. Blend well at speeds high enough to partially freeze mixture as ice particles become crushed and fine to form a thick slurry the consistency of a milk shake.

The above milk shake-like product without further embodiments has a very pleasant taste, although any desired combination of fruits, nuts, sweeteners, flavorings, seasonings, spices, fillers, extenders, binders, and so forth may also be added to the product.

Alternatively, the milk shake-like product may be formed by 152.4 g flour, 453 g water and 12.5 g oil (½ water and flour still cooked as described above) under conditions of simultaneous freezing and mixing to form a milk shake-like slurry without adding crushed ice.

Similarly other methods of the art may be used to produce the frozen slurry.

EXAMPLE NUMBER 22

True Yam Ice Cream

The milk shake-like product described in example 21 may be used as a base for ice cream products. The above slurry is subjected to freezing from 32 F to −30 F or lower, preferably—20–0 F., until product attains this temperature. Frozen mixture is then pulverized, and placed in high speed blending equipment and blended at highest speeds until well mixed, smooth, and creamy. FreeZing, pulverizing and mixing cycles may be repeated as desired, 2 such cycles are preferred. Additional embodiments described in Example 21 may also be used in this example.

EXAMPLE NUMBER 23

True Yam Noodles

Using conventional equipment for kneading thick dough, combine 453 g frozen flour from cooked tubers and 453 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors o the like. Dough may be used to make any pasta product common in the art including but not limited to ravioli, Chinese-style meat filled noodle dumplings, and other meatfilled products.

Alternatively a small amount of flour and water, preferably 20 g. true yam flour and 120 g water may be cooked to a thick paste and added to the above mixture.

In another alternative process, prior to extruding, the flour mixture described above which may or may not be simultaneously kneaded, may be maintained at temperatures above 50 C. for 2–30 minutes, preferably 2–5 minutes at 95 C. to gelatinize part of all of the dough.

When cooking, immerse noodles in boiling water for 30 seconds. Any other cooking techniques of the art may also be used. Noodles may be used in any type pasta dish—soups, stews, pasta and sauce dishes, and the like.

EXAMPLE NUMBER 24

True Yam Crackers

In any suitable machine for mixing heavy doughs, combine 453 g flour of cooked true yam flour, 340–453 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350 F. for 20 minutes. Otherwise, cook by any convention of the art, including baking, frying and the like.

Alternatively, omit oil, or oil and salt, increasing water by 30 grams.

Alternatively, use binders, flours, sweeteners, extenders, flavorings, seasonings, fillers and other ingredients common to the art to produce a hyperallergenic cracker.

EXAMPLE NUMBER 25

Pudding

Combine equal parts of cooked, mashed true yam paste and water, using 113.25 g each. The method forming the paste involves processes of cooking and pureeing by any conventional means including but not limited to steam heat, boiling and pressure cooking. Th preferred method involves subjecting the peeled or unpeeled raw tubers, peeled tubers are preferred, to application of steam until all starch particles are gelatinized. The gelatinized tubers are comminuted to a thick paste by any conventional means. Separately 5.3 g true yam flour is combined with 28.2 g water and heated to boiling point for 5 minutes to produce a thick gelatinized paste. The gelatinized paste is combined with the cooked tuber and water mixture by any conventional mixing technique until well blended. The mixture is the consistency of pudding and with the addition of no other ingredients has a pleasant, sweet taste. This is not to preclude the use of other ingredients commonly used as ingredients in pudding such as eggs, milk, conventional flours, oil, sweeteners, flavorants, spices, seasonings, of any kind in this invention.

Alternatively, 226 g water and 21.2 g flour may be heated until starchy materials are gelatinized, and pureed with conventional techniques until smooth and well blended. Cool to 0–20 C., preferably 5–10 C., when forms pudding consistency.

EXAMPLE NUMBER 26

Uncooked Flour of True Yam

Peeled tubers of the family Dioscoreacae are pulverized, comminuted, or pureed, or otherwise prepared for dehydration by low temperature e g freeze drying or vacuum-drying techniques. The dried tubers are pulverized to a fine flour by any grinding process that does not heat the flour high enough to cause a bitter taste, preferably a rolling ball mill or short residence time grinder. The whole peeled tuber is ground including all fibrous material, at least 10% fibrous, preferably 100%.

EXAMPLE 27

Flour of Cooked Tubers of True Yam

The tubers are peeled, and the like while being held under running water. They are then rinsed in distilled water, cut into cubes of any size, preferably 2×2×2, and subjected to heat with steam until thoroughly gelatinized. The tubers are then trimmed to remove all black, grey, or otherwise discolored sections, shredded to sizes approximately 2 inches long ×¼ inch wide ×⅛ inch thick. Place on glass trays and air dry at 145 F. for about 12 hours. The dried product is then pulverized to flours of various particle size distribution in any conventional grinding process that does not elevate the flour temperature above 100 C. Preferably, the entire tuber is ground including fibrous particles.

Having now fully described the invention, it will be apparent to one of ordinary skill in the art that many changes and modifications can be made thereto without departing from the spirit of the invention as set forth herein.

What is claimed as new and so intended to be secured by Letters Patent Is:

1. A non-grain, non-bitter edible yam flour possessing the ability to maintain a risen structure in the absence of grain flour, legume flour, or added fiber; said nongrain edible flour consisting of comminuted particles of the entire true yam of family Dioscoreaceae including substantially all of the starch and fibrous portions of the true yam, comminuted to a size so that all of said particles pass through a screen of 0.02 inch mesh, wherein said flour has a moisture content of less than 20% by weight.

2. The non-bitter entire flour of claim 1, wherein the flour passes through a screen of 0.001 inch mesh.

3. An infant formula consisting essentially of yam flour and water, wherein the yam flour consists of the flour of claim 1.

4. An imitation nut butter consisting essentially of yam flour and oil, wherein the yam flour consists of the flour of claim 1.

5. A milk substitute consisting essentially of yam flour and water, wherein the yam flour consists of the flour of claim 1, and wherein the flour and water are present in proportions of 1:1 to 1:30 parts by weight of flour per weight of water.

6. An ice cream substitute formed by a process comprising freezing the milk substitute of claim 5.

7. The non-grain, non-bitter flour of claim 1 wherein the yam flour is cooked.

8. The non-grain, non-bitter flour of claim 1 wherein the yam flour is uncooked.

9. A baked product consisting essentially of yam flour, water and leavening agent; wherein the yam flour consists of the flour of claim 1; and wherein the flour is present in an amount of 1 part by weight and the water is present in an amount of 0.5–4 parts by weight per weight of flour.

10. A colloidal product consisting essentially of yam flour, oil and water, wherein the yam flour consists of the yam flour of claim 1 and wherein flour is present in an amount of 0.1–3 parts by weight and the oil and water are each present in an amount of 1–15 parts by weight which may be the same or different.

11. A fried product consisting essentially of yam flour, oil and water wherein the yam flour consists of the flour of claim 1.

12. An extruded product consisting essentially of yam flour and water wherein the yam flour consists of the flour of claim 1.

13. A batter-type product consisting essentially of yam flour, oil and water, wherein the yam flour consists of the flour of claim 1, and wherein the yam flour is present in an amount of 1 part by weight; and the water is present in an amount of 0.5–6 parts by weight; and the oil is present in an amount of 0–$\frac{1}{3}$ part by weight.

14. An edible, cooked, non-bitter flour of true yams of family Dioscoreaceae having a particle size less than 0.02 inch mesh and a moisture content of less than 20% by weight, said flour produced by the process consisting essentially of the steps of:
gelatinizing the tuber with steam,
drying said true yams at temperatures not exceeding 145° F. such that a bitter taste is not introduced,
comminuting the entire dried true yam of the previous step, including substantially all of the starch and fibrous portions of the true yam, at temperatures not exceeding 100° C. so that a bitter taste is not introduced, and to a size so that the entire true yam will pass through a screen of 0.02 inch mesh, and,
recovering an edible no-bitter flour of true yam having a moisture content of less than 20% by weight.

15. A non-grain edible flour of true yams of the family Dioscoreaceae wherein the flour consists of the entire true yam, including all of the starch and fiber portions of said yam, comminuted to a size so that the comminuted yam will pass through a screen of 0.002 inch mesh, said flour having a moisture content less than 20%.

16. An edible, uncooked, non-bitter flour of true yams of family Dioscoreaceae having a particle size less than 0.02 inch mesh and a moisture content of less than 20% by weight, said flour produced by the process consisting essentially of the steps of:
drying uncooked true yams by freeze drying so that bitter taste is not introduced;
comminuting the entire dried true yam of the previous step including substantially all of the starch and fibrous portions of the true yam, at a temperature insufficient to introduce a bitter taste, and to a size so that the entire true yam will pass through a screen of 0.02 inch mesh; and,
recovering an edible non-bitter flour of said true yam having a moisture content of less than 20% by weight.

* * * * *